(12) United States Patent
LoPiccolo et al.

(10) Patent No.: US 12,733,942 B2
(45) Date of Patent: Sep. 15, 2026

(54) REAMING GUIDE SYSTEM AND METHOD FOR USING SAME

(71) Applicant: Howmedica Osteonics Corp., Mahwah, NJ (US)

(72) Inventors: Frank LoPiccolo, North Bergen, NJ (US); Justin Moidel, Verona, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

(21) Appl. No.: 19/186,043

(22) Filed: Apr. 22, 2025

(65) Prior Publication Data

US 2025/0325285 A1 Oct. 23, 2025

Related U.S. Application Data

(60) Provisional application No. 63/636,956, filed on Apr. 22, 2024.

(51) Int. Cl.
*A61B 17/17* (2006.01)

(52) U.S. Cl.
CPC ................................ *A61B 17/1764* (2013.01)

(58) Field of Classification Search
CPC .................................................. A61B 17/1764
See application file for complete search history.

(56) References Cited

U.S. PATENT DOCUMENTS

| | | | |
|---|---|---|---|
| 6,074,392 A | 6/2000 | Durham | |
| 8,961,516 B2 | 2/2015 | Nelson et al. | |
| 9,522,008 B2 | 12/2016 | Ferko et al. | |
| 11,123,085 B2 | 9/2021 | Servidio et al. | |
| 2006/0264952 A1 | 11/2006 | Nelson et al. | |
| 2014/0276859 A1* | 9/2014 | Chaney .............. | A61B 17/1764 606/88 |

FOREIGN PATENT DOCUMENTS

WO 9427507 A1 12/1994

* cited by examiner

*Primary Examiner* — Sameh R Boles
(74) *Attorney, Agent, or Firm* — Lerner David LLP

(57) ABSTRACT

A system includes a hollow reamer and an alignment instrument. The alignment instrument includes a shaft contoured to receive the hollow reamer such that the hollow reamer is translatable therealong. The alignment instrument further includes an articulation component coupled to the distal end of the shaft and a stem coupled to the articulation component. The shaft is configured to articulate relative to the articulation component. Further, the shaft includes a movable component configured to transition the alignment instrument between an unlocked state and a locked state via contact between the movable component and the articulation component. In the unlocked state, the articulation component is configured to articulate with respect to the shaft. In the locked state, the articulation component is configured to be fixed relative to the shaft.

9 Claims, 8 Drawing Sheets

REAMING GUIDE SYSTEM AND METHOD FOR USING SAME

CROSS-REFERENCE TO RELATED APPLICATIONS

This application claims the benefit of the filing date of U.S. Provisional Patent Application No. 63/636,956 filed Apr. 22, 2024, the disclosure of which is hereby incorporated herein by reference.

BACKGROUND

In surgeries which require reaming of an interior portion of a bone, such as a total knee arthroplasty (TKA), a cone-shaped reamer may be used to ream the interior portion of a tibia or femur and prepare the bone for a corresponding tibial or femoral component. To aid the guidance of the reamer, some surgical procedures may include a guide such as a rod. In such instances, the reamer may be cannulated so that the reamer may be advanced along the guide to cut the bone in a controlled manner. A rigid linear rod can be inserted straight into an intramedullary canal of the long bone or at an angle with respect to an axis of the canal upon initial insertion. However, as the rod is advanced further into the intramedullary canal, the decreasing radius or width of the canal forces the rod alignment to converge with the axis of the canal, thereby limiting the ability to use the guide at a desired angle relative to a length direction of the long bone being cut. Specifically, the structure of the rod limits the angle at which the reamer can be advanced through the canal and thus limits the desirable portion of the bone that can be reamed.

Accordingly, improvements in instrumentation to provide a greater number of options for controlled reaming at an end of a long bone in surgical procedures are desirable.

BRIEF SUMMARY

In one aspect, the present disclosure describes an alignment instrument designed to receive a cone reamer. The instrument is adjustable to match the functional position of a femoral or tibial component placed during a TKA, whether the component is a trial or an implant. A trailing component of the instrument is actuatable with respect to the leading component to set a cutting path for the reamer, and is lockable once a desired angle is established. In some embodiments, the alignment instrument includes a shaft and a stem coupled to a distal end of the shaft and is configured to articulate with three degrees of freedom with respect to the stem. The shaft is additionally lockable with respect to the stem to prevent articulation of the shaft with respect to the stem. The alignment instrument described herein may be used to align and stabilize the path followed by the cone reamer during a manual surgery or a surgery performed with the aid of robotics. In a method of using the alignment instrument, a leading component of the instrument is advanced into the intramedullary canal of a long bone, such as a femur or tibia, causing the leading component to align with the surfaces of the canal and become press fit into the canal, thereby providing stability. Thus, in surgery, a surgeon may insert the stem of the instrument into the intramedullary canal of a long bone, adjust the angle of the shaft with respect to the stem to a desirable reaming angle while relying on the interior of the long bone to hold the stem in place, and then lock the shaft relative to the stem when the shaft is in a desirable orientation to prevent the shaft from moving while the instrument is used as a guide to advance the reamer.

According to a first aspect of the disclosure, a system may include a hollow reamer and an alignment instrument. The alignment instrument may include an outer shaft, an inner shaft, an articulation member, and a stem. The inner shaft may be disposed in the outer shaft and may be translatable within the outer shaft. The articulation member may include a ball component and an extension component extending from the ball component. The ball component may be enclosed within an end portion of the outer shaft. The stem may be attached to the extension component. Translation of the inner shaft relative to the outer shaft may control locking of the outer shaft relative to the stem. When the outer shaft is locked relative to the stem, an angle between a central longitudinal axis of the outer shaft and a central longitudinal axis of the stem may be fixed. When the outer shaft is unlocked relative to the stem, the angle between the central longitudinal axis of the outer shaft and the central longitudinal axis of the stem may be adjustable. The outer shaft of the alignment instrument may have an outer surface contoured to slidably receive a hollow reamer such that when the alignment instrument is disposed in a bone cavity of a bone, the hollow reamer may be advanceable over the alignment instrument to cut the bone along a position and orientation of the alignment instrument.

Further in the first aspect of the disclosure, the system may include an alignment block which may be disposable over the outer shaft of the alignment instrument. The alignment block may have a distal surface configured to align the outer shaft based on an external proximal surface of the bone. The stem may have an outer surface contoured to slidably receive the hollow reamer such that when the alignment instrument is disposed in a bone cavity of a bone, the hollow reamer may be advanceable over an entirety of the alignment instrument to cut the bone along a position of the alignment instrument. The cap may define a proximal opening sized and shaped to correspond to a distal portion of the shaft. The cap may include a lip at a distal end defining a bore sized and shaped to receive the extension component therethrough. The stem may be threadably coupled to the extension component. The inner shaft may include a threaded portion at a distal end thereof adapted to contact the ball component to lock the articulation member. The inner shaft may include a rotation portion at a proximal end thereof adapted for actuating the inner shaft relative to the outer shaft. The ball component may be received within an end socket of the outer shaft. The end socket of the outer shaft may include a cap threadably coupled to a distal portion of the outer shaft, and the ball component may be disposed between the cap and the distal portion of the outer shaft. A kit may include the system according to the first aspect described above and a plurality of stems. At least two stems of the plurality of stems may have different lengths. Each stem of the plurality of stems may be adapted to attach to the extension component.

According to a second aspect of the disclosure, a method of preparing a long bone for reaming may include retrieving an alignment instrument. The alignment instrument may include an outer shaft, a stem, and an inner shaft. The stem may be attached to the outer shaft via a joint member such that the outer shaft is rotatable relative to the stem. The inner shaft may be movably disposed in the outer shaft. The method may further include advancing the alignment instrument at least partially into an intramedullary canal of the long bone, the stem being at a leading end of the alignment instrument; moving the inner shaft relative to the outer shaft to lock an angulation of the outer shaft relative to the stem; advancing a hollow reamer over the outer shaft; and reaming a portion of the long bone with the hollow reamer along the outer shaft while the angulation of the outer shaft is fixed relative to the stem disposed within the intramedullary canal.

Further in the second aspect of the disclosure, the method may further include adjusting an orientation of the outer shaft relative to the stem prior to locking the angulation. The method may further include advancing an alignment block over the outer shaft prior to adjusting the orientation of the outer shaft and aligning a surface of the alignment block with a resected surface on an elongate end of the long bone, thereby aligning the outer shaft based on the resected surface. The method may further include resecting the resected surface on the elongate end of the long bone to form the resected surface along a plane adapted to abut the alignment block and orient the alignment block at a desired angle. Advancing the alignment block over the outer shaft may include positioning the alignment block over the outer shaft such that the outer shaft is passed through a bore defined by the alignment block. The outer shaft may extend along a first axis and the bore may extend along a second axis, and the first and second axes may be coincident when the alignment block is advanced along the alignment block. The stem may be a first stem and the method may further include decoupling the first stem from the outer shaft and attaching a second stem to the outer shaft, the second stem being different from the first stem. The second stem may have a length different from the first stem.

According to a third aspect of the disclosure, an alignment instrument configured for use in a long bone may include an outer shaft, an inner shaft, an articulation component, and a stem. The outer shaft may extend from a first end to a second end along a first central longitudinal axis. The outer shaft may be configured to receive a hollow reamer thereon such that the hollow reamer is translatable along a length direction of the shaft. The inner shaft may be movably disposed within the outer shaft. The articulation component may be coupled to the second end of the shaft and may be configured to articulate relative to the shaft. The stem may be coupled to the articulation component and may extend from a first end to a second end along a second central longitudinal axis. The articulation component may be configured to transition between an unlocked state and a locked state based on a position of the inner shaft relative to the outer shaft. In the unlocked state, the articulation component may be configured to articulate with respect to the shaft. In the locked state, the articulation component may be configured to be fixed relative to the shaft.

Further in the third aspect of the disclosure, the alignment instrument may include a cap threadably coupled to the second end of the outer shaft to couple the articulation component to the shaft. The cap may extend from a first end to a second end and the cap may define an opening at the first end sized to correspond to a threaded portion of the outer shaft. An interior surface of the cap may be threaded, and the interior surface of the cap may be adapted to threadably couple to an exterior surface of the threaded portion of the outer shaft. The cap may include a lip extending radially inwardly at the second end of the cap, and the lip may be configured to engage with the articulation component to retain the articulation component within the shaft. The articulation component may include a ball component and an extension component extending from the ball component, and the second end of the cap may define a bore radially inward of the lip adapted to receive the extension component therethrough. Rotation of the inner shaft relative to the outer shaft may be configured to transition the alignment instrument between the locked state and the unlocked state.

Further in the third aspect of the disclosure, the articulation component may include a ball component and an extension component extending from the ball component, and the inner shaft may include a threaded end portion at an end thereof, the threaded end portion being movable relative to the outer shaft such that the threaded end portion is movable to protrude beyond the second end of the outer shaft and to press against the ball component. The inner shaft may include a rotation portion at an end protruding beyond the first end of the outer shaft, and the rotation portion may be configured to be handled by a user to rotate the inner shaft relative to the outer shaft to move the inner shaft along the first central longitudinal axis relative to the outer shaft. The stem may be configured to couple to the extension component. The stem may include a threaded interior bore along the second central longitudinal axis extending from the first end of the stem, and the threaded interior bore may be configured to be threadably coupled to the extension component. The articulation component may be received within an end socket of the shaft. The end socket may be enclosed by a cap coupled to the shaft. The articulation component may be at least partially enclosed between the cap and the shaft. A system may include the alignment instrument according to the third aspect of the disclosure and an alignment block. The alignment block may define a central bore sized and shaped to receive the shaft of the alignment instrument. The alignment block may include a side adapted to contact a first surface of a resected bone to set an orientation of the shaft of the alignment instrument with respect to the bone, and the orientation may be predetermined based on an angle between the central bore and a plane through the side of the alignment block. The outer shaft may include an interior threaded surface adapted to engage with a threaded portion of the inner shaft.

According to a fourth aspect of the disclosure, an alignment instrument configured for use in a long bone may include an adjustable shaft, an articulation component, and a stem. The adjustable shaft may extend from a first end to a second end along a first central longitudinal axis. The adjustable shaft may be configured to receive a hollow reamer thereon such that the hollow reamer is translatable along a length direction of the adjustable shaft. The articulation component may be coupled to the second end of the shaft and may be configured to articulate relative to the adjustable shaft. The stem may be coupled to the articulation component and may extend from a first end to a second end along a second central longitudinal axis. The articulation component may be configured to transition between an unlocked state and a locked state based on a position of the adjustable shaft. In the unlocked state, the articulation component may be configured to articulate with respect to the adjustable shaft. In the locked state, the articulation component may be configured to be fixed relative to the adjustable shaft.

Further in the fourth aspect of the disclosure, the adjustable shaft may be configured such that the position of the adjustable shaft may include a first position and a second position. The first position may place the articulation component in the unlocked state and the second position may place the articulation component in the locked state. A portion of the adjustable shaft may move to transition between the first and second positions. The adjustable shaft may further include an outer cannulated shaft and an inner shaft. The outer cannulated shaft may extend from a first end to a second end along the first central longitudinal axis. The inner shaft may be configured to be disposed within the outer shaft. The inner shaft may extend along the first central longitudinal axis when the inner shaft is disposed within the cannulated outer shaft.

DETAILED DESCRIPTION

As used herein, the term "proximal," when used in connection with a device, e.g., instrument, or components of a device, refers to the end of the device closer to the user of the device (e.g., surgeon or operator) when the device is being used as intended. On the other hand, the term "distal," when used in connection with a device or components of a device, refers to the end of the device farther away from the user when the device is being used as intended. As used herein, the term "superior" means closer to the head of a person relative to another location of the person while on the other hand, the term "inferior" means closer to the feet of a person relative to another location on the person. It should be understood that these terms are not limiting, but merely used for ease of description, and that varied orientations may cause directions to differ.

As used herein, the terms "about," "generally," "approximately," and "substantially" are intended to mean that slight deviations from absolute are included within the scope of the term so modified. However, unless otherwise indicated, the lack of any such terms should not be understood to mean that such slight deviations from absolute are not included within the scope of the term so modified.

In one aspect, the present disclosure relates to an instrument used for alignment of a reamer used to prepare a bone for receipt of an implant during surgery. However, it should be noted that the instrument is not limited to use in surgery and may be used for the alignment of objects in any context, particularly the alignment of hollow or cannulated cutting tools. By way of example only, the instrument can be employed to implant a wide array of cone-shaped medical implants where an instrument is used to prepare a cone cavity for the implant. The instrument allows alignment of a cone reamer with an implantation orientation of an implant, such as a tibial or femoral component used in a TKA revision. The instrument includes a shaft adapted to articulate relative to a stem when in an unlocked condition and that is fixable relative to the stem in a locked condition. The ability to stabilize the cone reamer and allow for pivotable adjustment of the shaft about its attachment to the stem so that the shaft is aligned with a planned functional implant position provides improved precision of implant placement and provides improved correspondence of the bone and implant interface.

Figures 1, 2, 3:
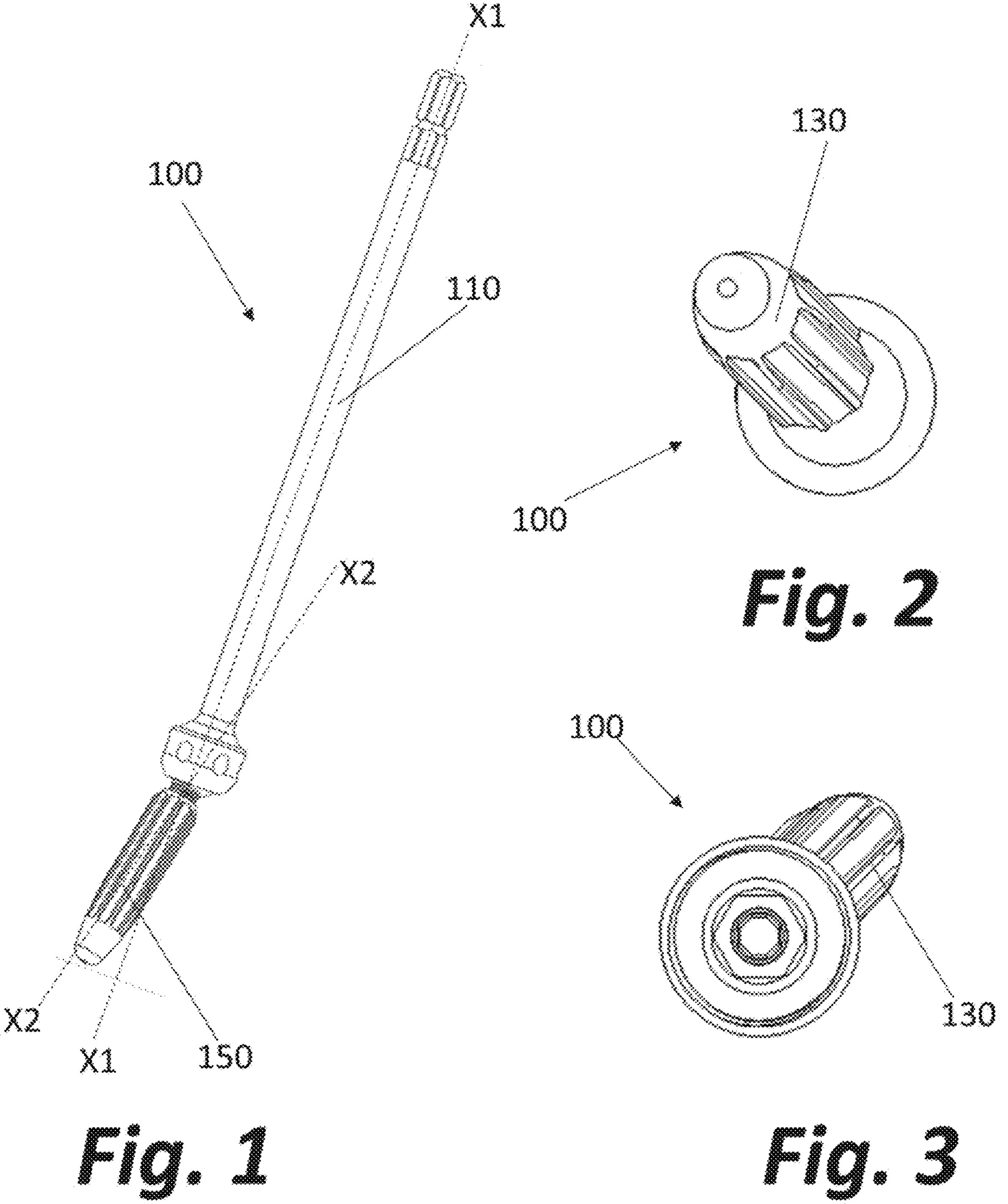
FIG. 1 is a perspective view of an alignment instrument according to an embodiment of the disclosure.
FIG. 2 is a bottom view of the alignment instrument of FIG. 1.
FIG. 3 is a top view of the alignment instrument of FIG. 1.
Figure 4:
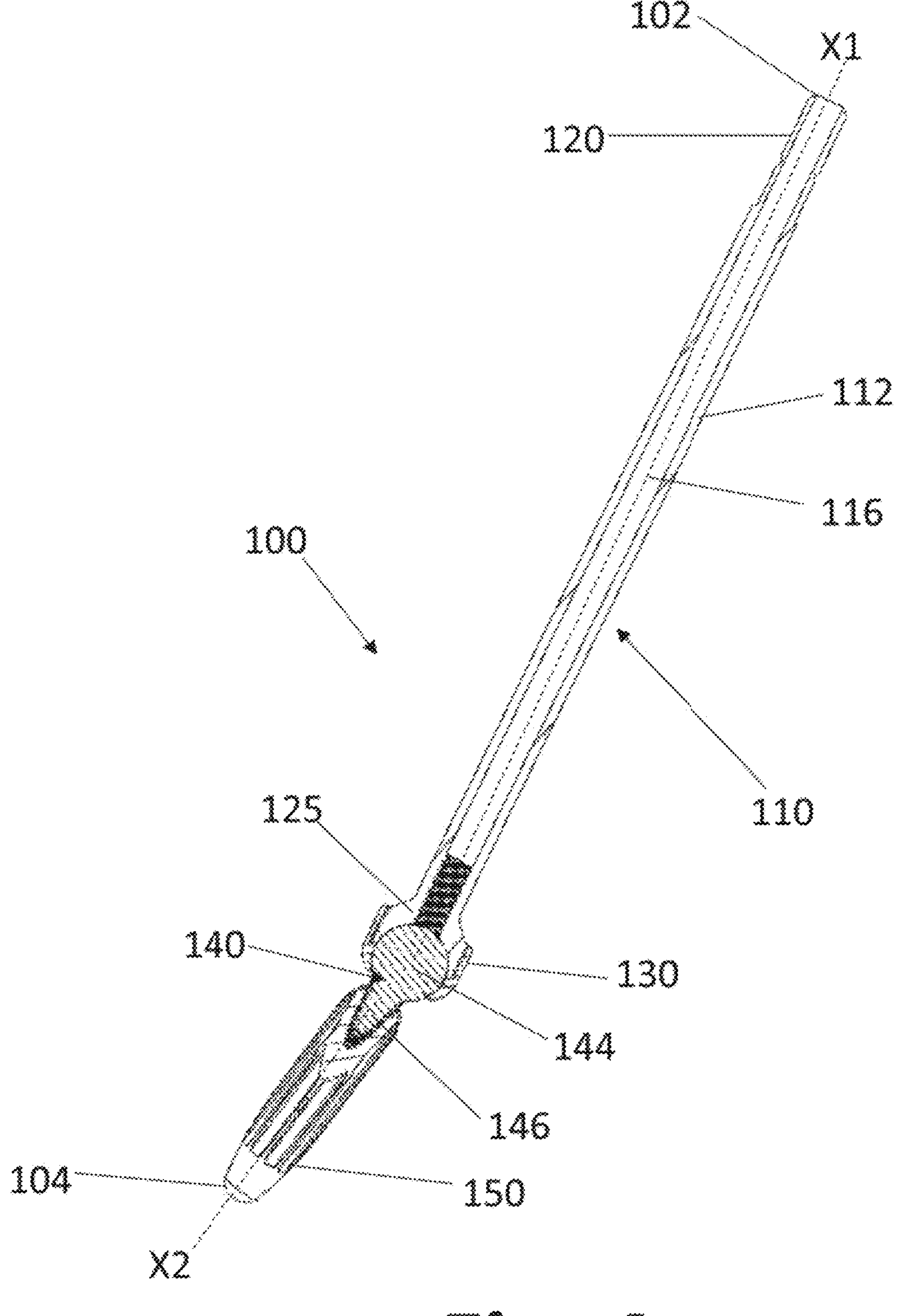
FIG. 4 is a cross-sectional side view of the alignment instrument of FIG. 1.
Figure 5:
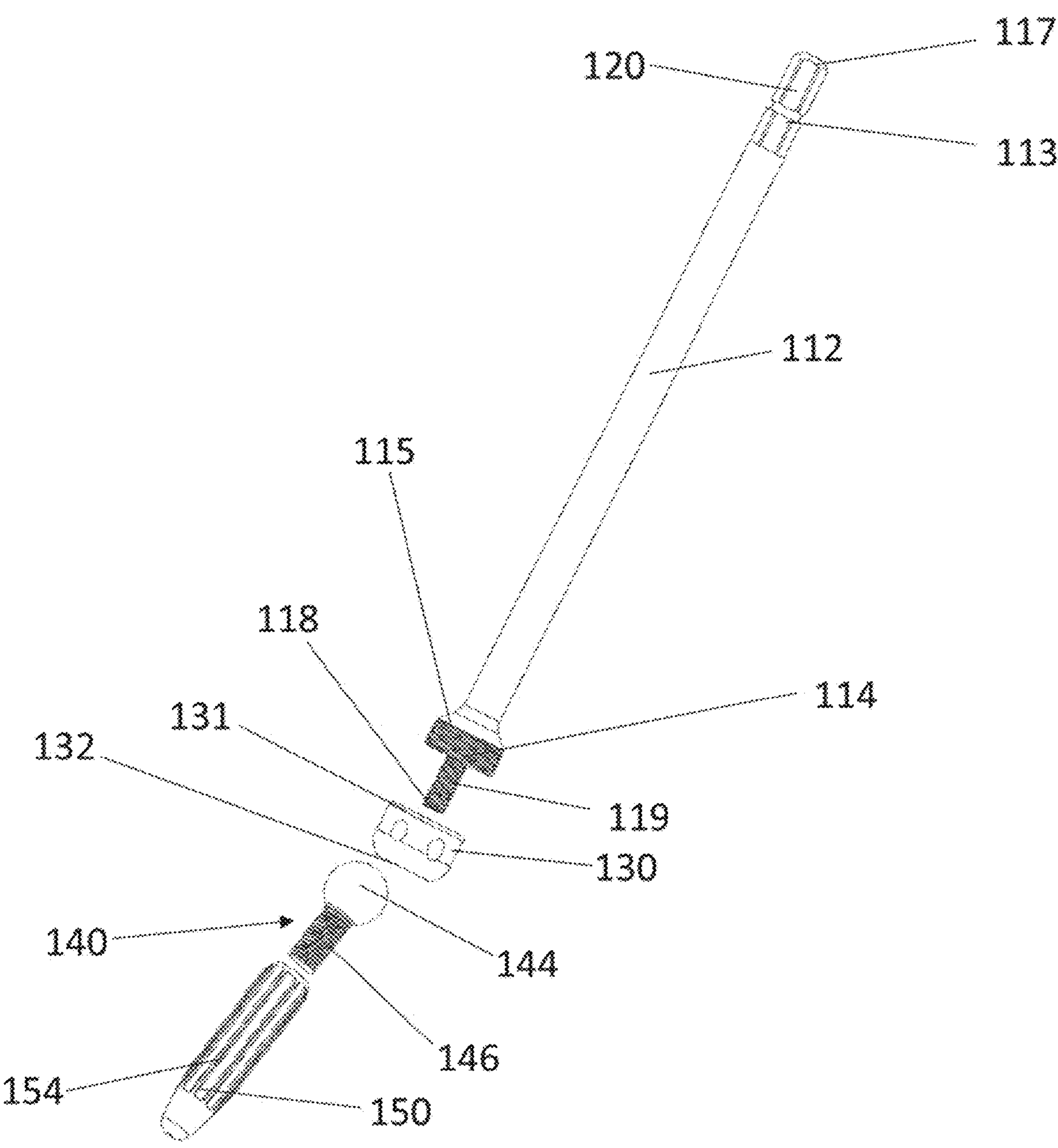
FIG. 5 is an exploded view of the alignment instrument of FIG. 1.

FIGS. 1, 4 and 5 illustrate an alignment instrument 100 according to one embodiment of the present disclosure. Alignment instrument 100 has a length that extends from a proximal end 102 to a distal end 104 and includes a shaft 110, a cap 130, an articulation component 140 and a stem 150. Stem 150 is coupled to shaft 110 at a joint formed by the combination of articulation component 140 and cap 130 as described below in greater detail. Shaft 110 has an elongate dimension that extends from proximal end 102 of alignment instrument 100 along a central longitudinal axis X1 to a distal end forming part of the joint. Shaft 110 includes and collectively refers to a cannulated outer shaft 112 and an inner shaft 116 disposed within the outer shaft.

Outer shaft 112 is shown in FIGS. 4 and 5 while inner shaft 116 is shown disposed in outer shaft 112 in FIG. 5. Outer shaft 112 is cannulated and extends from a proximal end 113 to a distal end 114 along central longitudinal axis X1. Outer shaft 112 includes internal threads on an interior surface of the outer shaft that defines the cannulation, such internal threads extending from distal end 114 over a distal end portion of the interior surface. Outer shaft 112 may have a first outer diameter along a substantial portion of a length of the outer shaft. Further, an outer surface of outer shaft 112 may be contoured to receive a hollow reamer thereon. For example, the first outer diameter of outer shaft 112 may correspond closely to an inner diameter of a hollow or cannulated reamer which may be applied thereon during the reaming process. In such an arrangement, the outer diameter of outer shaft 112 may be only marginally smaller than the inner diameter of the hollow reamer to allow for translation of the reamer relative to the shaft, while ensuring a snug fit between the elements. In this manner, the reamer is operable in a stable manner while slidably disposed over the outer shaft. In some examples, the outer surface of outer shaft 112 may be smooth along its length, as shown in FIG. 1. In still further examples, outer shaft 112 may have an outer surface that varies from that shown in FIG. 5 while still having a contour suitable to facilitate the slidable disposal of a cutting tool thereon, such as a reamer. A distal portion 115 of the outer shaft flares radially outward to a second diameter greater than the first outer diameter. Distal portion 115 defines end socket 125 that is in direct communication with the cannulation of the outer shaft. An external surface of end socket 125 includes external threads as shown in FIG. 5 to allow for threadable engagement with cap 130.

Inner shaft 116 extends from a proximal end 117 to a distal end 118 along central longitudinal axis X1 and has an outer diameter smaller than an inner diameter of outer shaft 112 to be movably disposable therein. Inner shaft 116 further includes a rotation portion 120 at proximal end 117 and a threaded portion 119 at distal end 118. Threaded portion 119 is externally threaded and extends from distal end 118 over a distal end portion of inner shaft 116. In an assembled condition, i.e. when ready for use in a surgical procedure, a substantial portion of inner shaft 116 is disposed within outer shaft 112 with only rotation portion 120 and threaded portion 119 being exposed, as shown in FIG. 5. That is, when inner shaft 116 is disposed within outer shaft 112 during use of alignment instrument 100, rotation portion 120 protrudes beyond proximal end 113 of outer shaft 112 and threaded portion 119 protrudes beyond distal end 114 of outer shaft 112. The external threads of threaded portion 119 extend along a sufficient portion of a length of inner shaft 116 so as to engage and cooperate with the internal threads of outer shaft 112. In this manner, inner shaft 116 is rotatable relative to outer shaft 112 to advance or retract inner shaft 116 relative to outer shaft 112 while also remaining engaged to outer shaft 112. Further, inner shaft 116 is rotatable within outer shaft 112 to an extent such that threaded portion is advanceable until it protrudes distally beyond distal end 114 of the outer shaft.

Figure 6:
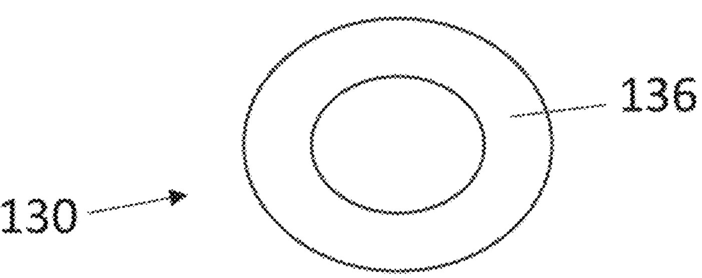
FIG. 6 is a top view of a cap of the alignment instrument of FIG. 1.
Figure 7:
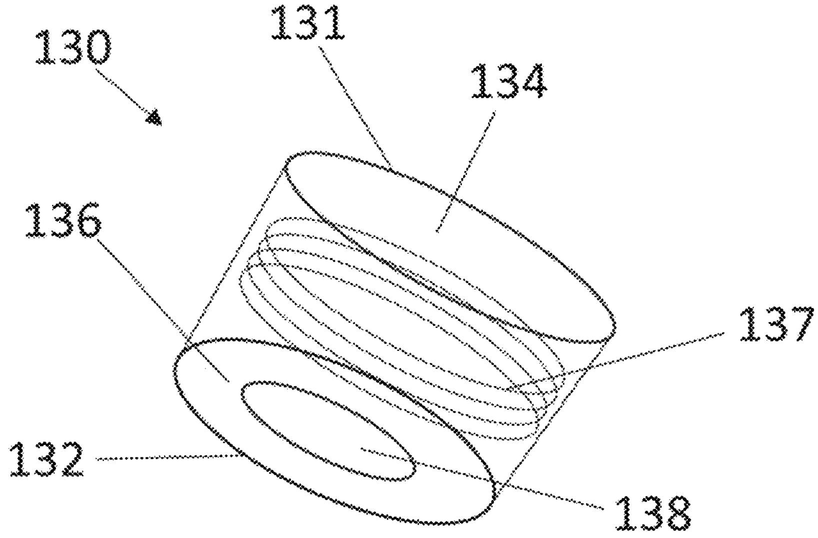
FIG. 7 is a perspective view of the cap of FIG. 6.

Cap 130 has a hollow, generally cylindrical shape extending a length from an open end 131 to a closed end 132. A top view of cap 130 is shown in FIG. 6 and FIG. 7 is a perspective view of the cap wherein the cap is shown transparent to illustrate the threading included on the interior surface. Cap 130 is open-faced at open end 131 and is sized to be receivable on end socket 125 of outer shaft 112. Specifically, a threaded inner surface 137 of cap 130 complements the threaded outer surface of end socket 125 and facilitates threaded engagement between cap 130 and distal portion 115 of outer shaft 112. The internal threads of cap 130 may extend circumferentially around the inner surface and over a depth of the cap or in some examples, a portion of the depth. Cap 130 has an internal diameter corresponding to an outer diameter of distal portion 115 of outer shaft 112 such that the internal threads of the cap are sized and shaped to threadably engage the external threads on the external surface of the end socket 125 of the outer shaft. At closed end 132, cap 130 further includes a bore 138 defined by a circumferential lip 136 extending radially inwardly from a periphery of the cap such that the bore at the distal end of the cap is smaller than opening 134 at open end 131 of the cap. In other words, opening 134 defined at open end 131 of cap 130 has a first diameter and bore 138 at closed end 132 of the cap has a second diameter smaller than the first diameter. Cap 130 is configured to be coupled to distal portion 115 of outer shaft 112 so that the combined cap and end socket provide an enclosure for receiving articulation component 140 as described further below. When such articulation component 140 is received in the enclosure, a portion of the articulation component 140 is also passed through bore 138, again, described further below.

Articulation component 140, best shown in FIGS. 4 and 5, includes a ball component 144 and an extension component 146 extending from the ball component. Ball component 144 has a generally spherical-shape and extension component 146 may have, as depicted, a linear elongate dimension. Ball component 144 is sized and shaped such that the entirety of the ball component can be passed through opening 134 at open end 131 of cap 130, but only a portion of the ball component can be passed through bore 138 at closed end 132 of the cap. That is, the diameter of ball component 144 is greater than the diameter of the bore 138 at closed end 132 of cap 130. Put another way, a portion of ball component 144 that is less than a hemisphere may be able to pass through bore 138. This distal portion of ball component 144, e.g., a subportion of the ball component adjacent to extension component 146, has a smaller overall dimension across a width of the cap compared to a diameter of the ball component through a center of the ball component. Thus, when ball component 144 is coupled to cap 130 by passing the cap over the distal end of extension component 146 and advancing the cap proximally relative to articulation component 140, a portion of the ball component is reached that has a width as large as or larger than the diameter of bore 138 of the cap. At such a portion, ball component 144 will abut lip 136 of cap 130 and any remaining (e.g., relatively proximal) portion of the ball component will be prevented from passing through the bore of the cap. Ball component 144 is configured to articulate with three rotational degrees of freedom when the ball component is enclosed between cap 130 and end socket 125 of outer shaft 112.

Extension component 146 is cylindrical and externally threaded. Extension component 146 is sized and shaped to be received through bore 138 at closed end 132 of cap 130 as shown in FIG. 4. It should be appreciated that FIG. 4 is generally a cross-sectional view of alignment instrument 100, although while FIG. 4 illustrates a cross-section of shaft 110 and articulation component 140, a portion of stem 150 is shown as a side view. It should also be appreciated that inner shaft 116 is more clearly shown in FIG. 5. The diameter of bore 138 is greater than an outer diameter of extension component 144. As described above, extension component 144 is sized to pass through bore 138, and the extension component is able to articulate with three rotational degrees of freedom with respect to shaft 110 when enclosed via cap 130. As such, extension component 144 can be angled in a three-hundred-sixty-degree range of motion relative to axis X1 when the articulation component is coupled to shaft 110.

Stem 150 is elongate and as depicted, has a generally cylindrical-shape, though an outer shape of stem may vary to the extent it may still be advanced into an intramedullary canal of a patient and secure the instrument in the intramedullary canal. Stem 150 has a length from proximal end 151 to distal end 152. Stem 150 may have a diameter which remains consistent along a substantial length of the stem, but the diameter may taper near distal end 150 such that the stem may be bullet-shaped. Stem 150 may also have a plurality of elongate ridges 154, the ridges positioned side-by-side around an outer circumference of the stem with each ridge extending lengthwise along the outer circumference of the stem. Stem 150 has an interior bore at proximal end 151, the interior bore sized and shaped to correspond to extension component 146 of articulation component 140 such that the interior bore of stem is configured receive the extension component therein. The interior bore of stem 150 includes threading along its periphery, the threading sized and positioned to engage with and be threadably coupled to the external threading of extension component 146. While alignment instrument 100 is described with a single stem 150, it should be appreciated that instrument 100 may include a stem having a different size than stem 150 as shown. Further, instrument 100 is configured in a manner such that stem 150 may be detached from articulation component 140 and another stem may be threaded onto the instrument. Such feature is advantageous in that the instrument may be adapted for different patient anatomy or different needs in a specific procedure. The components of alignment instrument may be formed of a rigid material, such as stainless steel, titanium and the like.

Figure 9:
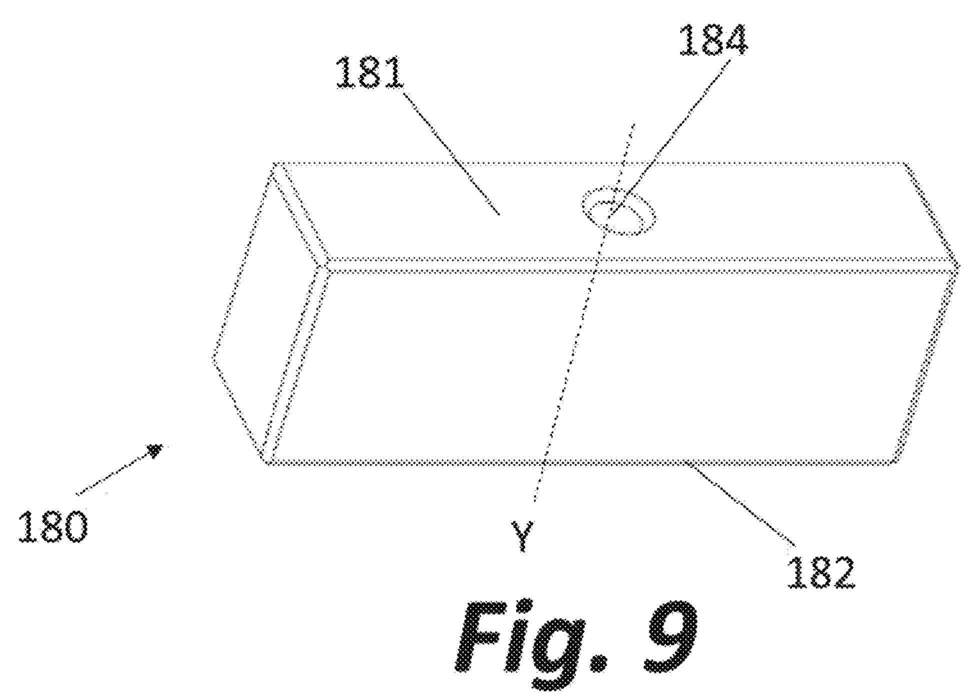
FIG. 9 is a perspective view of an alignment block according to an embodiment of the disclosure.

In one aspect, the present disclosure relates to a system that includes an alignment instrument and an alignment block. In one embodiment, a system may include alignment instrument 100 as shown in FIGS. 1 and 4-5 and alignment block 180 as shown in FIG. 9. Alignment instrument 100 may include any number of features as described elsewhere in the present application. As depicted, alignment block 180 is a rectangular prism with a height dimension extending from an upper side 181 to a bone-contacting side 182 and including a bore 184 extending therethrough along a bore axis Y between the upper and bone-contacting sides. Bore 184 is sized and shaped to receive shaft 110 of alignment instrument 100. Bore 184 may have a diameter which corresponds to the outer diameter of shaft 110 so that a snug fit may be formed when the shaft is positioned within the bore of alignment block 180, while still allowing alignment block 180 to slide over shaft 110. Alignment block 180 is configured to operate with alignment instrument 100 by passing bore 184 of alignment block 180 over outer shaft 112. In some examples, alignment block 180 may have different shapes and/or sizes. For example, the bone-contacting surfaces on some alignment blocks may be straight and/or flat, whereas the bone-contacting surfaces on other alignment blocks may be stepped, slanted or sloped (e.g., extending along a plane oblique to the bore axis). In further examples, the bore axis of some alignment blocks may be straight through the block (e.g., perpendicular to the upper surface and/or the bone-contacting surface) whereas the bore axis of other alignment blocks may be oblique to the upper and/or bone-contacting surface. Further detail regarding how the system is used is described in the method of using the system below.

The alignment instrument may be varied in many ways. In some examples, the stem may be provided in a size different from illustrated stem 150 to best fit and appropriately anchor within differently sized intramedullary canals. In further examples, a plurality of stem sizes, e.g., stems with different lengths and/or diameters, may be provided together with a single alignment instrument, and the interior bore of each included stem may be approximately the same size to threadably mate with the same articulation component so that the various sizes of stems are interchangeable on the single alignment instrument. It should be noted that the shapes of the components of the alignment instrument are not limited to the shapes described and illustrated herein, but may be modified while still accomplishing the same function as described above. In other examples, the ball portion of the articulation component and the inner surface of the cap may both be defined by a series of polygonal surfaces rather than a smooth surface. That is, instead of the ball component being a sphere, it may have a series of flat surfaces to define its outer surface, each separated by edges. In this manner, the shaft may be operated with slightly more resistance compared to a spherical ball joint while unlocked relative to the stem. In further examples, the cone reamer may be formed by a radially inner piece which directly contacts the shaft and a radially outer piece which rotates relative to the radially inner piece to ream bone. The outer shaft may include a spline or protrusion extending radially outward from its surface such that a shape of the outer shaft is non-cylindrical. The inner piece of the cone reamer may have a complementary shape to the outer shaft so that when the reamer is positioned on and advanced along the outer shaft, inward facing surface features on the inner piece of the reamer correspond to the protrusion on the periphery of the outer shaft to rotationally lock the inner piece of the cone reamer to the shaft while still allowing relative translational movement between the parts.

In one aspect, the present disclosure relates to a kit. A kit may include inner shaft 116, outer shaft 112, cap 130, articulation component 140, stem 150, and alignment block 180. It is further contemplated that a hollow cone reamer and an implant may be included in the kit. The kit may be provided with any and/or all of the above-noted components disassembled such that assembly is required by the surgeon upon receipt in the manner described throughout this disclosure. Alternatively, some or all of the pieces noted above may be provided already assembled in the kit, thereby reducing or eliminating the need for assembly by the surgeon. In some examples, a kit may be provided with a plurality of stems, which be the same size or different sizes, such as those having different diameters or lengths, and which may be interchangeably coupled to an articulation component provided in the kit. In other examples, a kit may be provided with a plurality of alignment blocks having different shapes and/or sizes. For example, the bone-contacting surfaces on some alignment blocks included in a kit may be straight and/or flat, whereas the bone-contacting surfaces on other alignment blocks may be stepped, slanted or sloped (e.g., extending along a plane oblique to the bore axis). In further examples, the bore axis of some alignment blocks may be straight through the block (e.g., perpendicular to the upper surface and/or the bone-contacting surface) whereas the bore axis of other alignment blocks may be oblique to the upper and/or bone-contacting surface.

In still further aspects, the present disclosure relates to a method of assembly and use of the alignment instrument. In some embodiments, the method may be directed to a method of assembly by itself. In other embodiments, the method may be directed to a method of use by itself. In still further embodiments, the method of assembly and the method of use may be performed as part of a single method, where the method of use is performed in sequence after completion of the assembly. One example of the method of assembly is shown in FIG. 11 and one example of the method of use is shown in FIG. 12.

Figure 11:
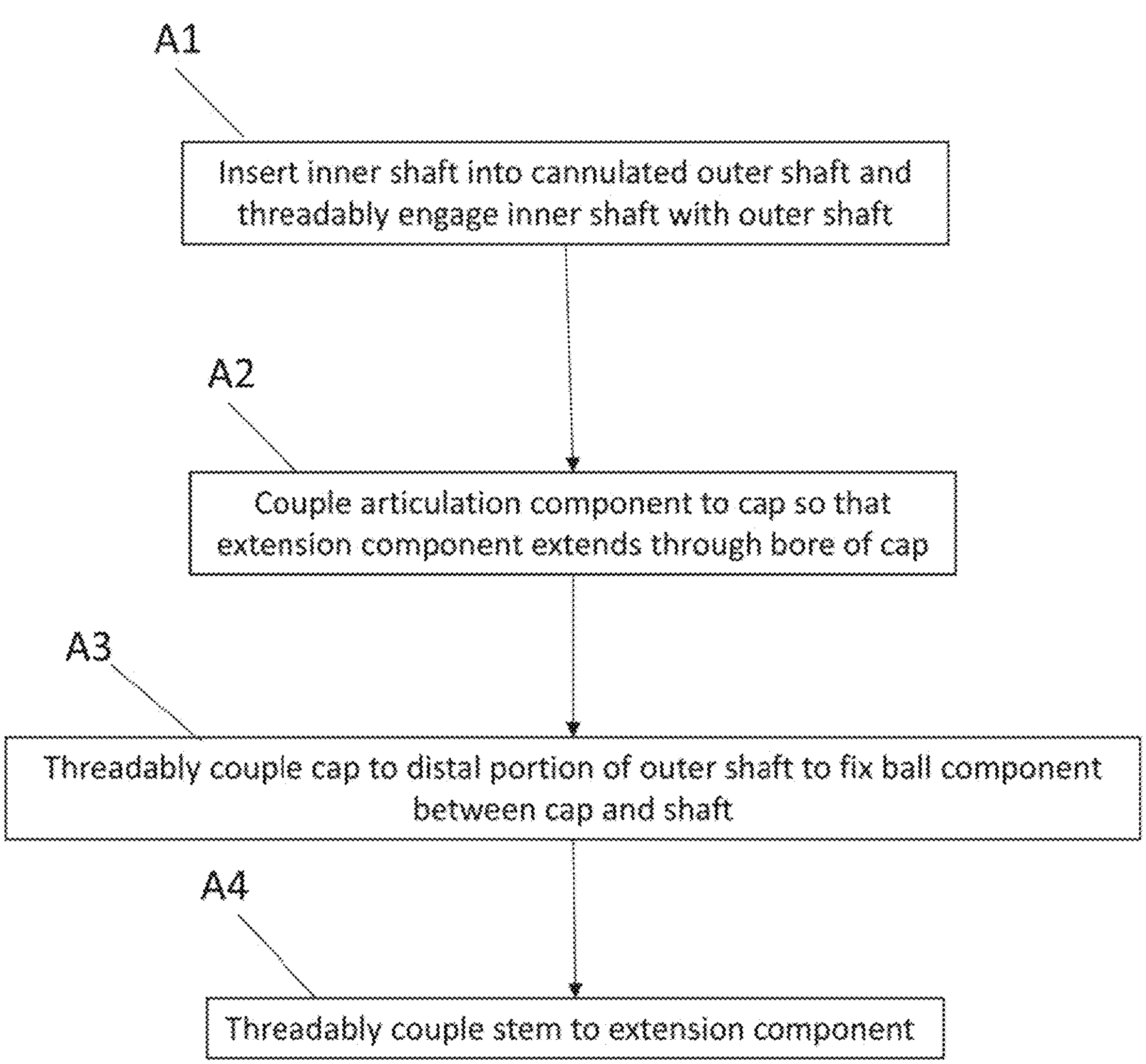
FIG. 11 is a flow chart illustrating a method of assembling the alignment instrument of FIG. 1.
Figure 12:
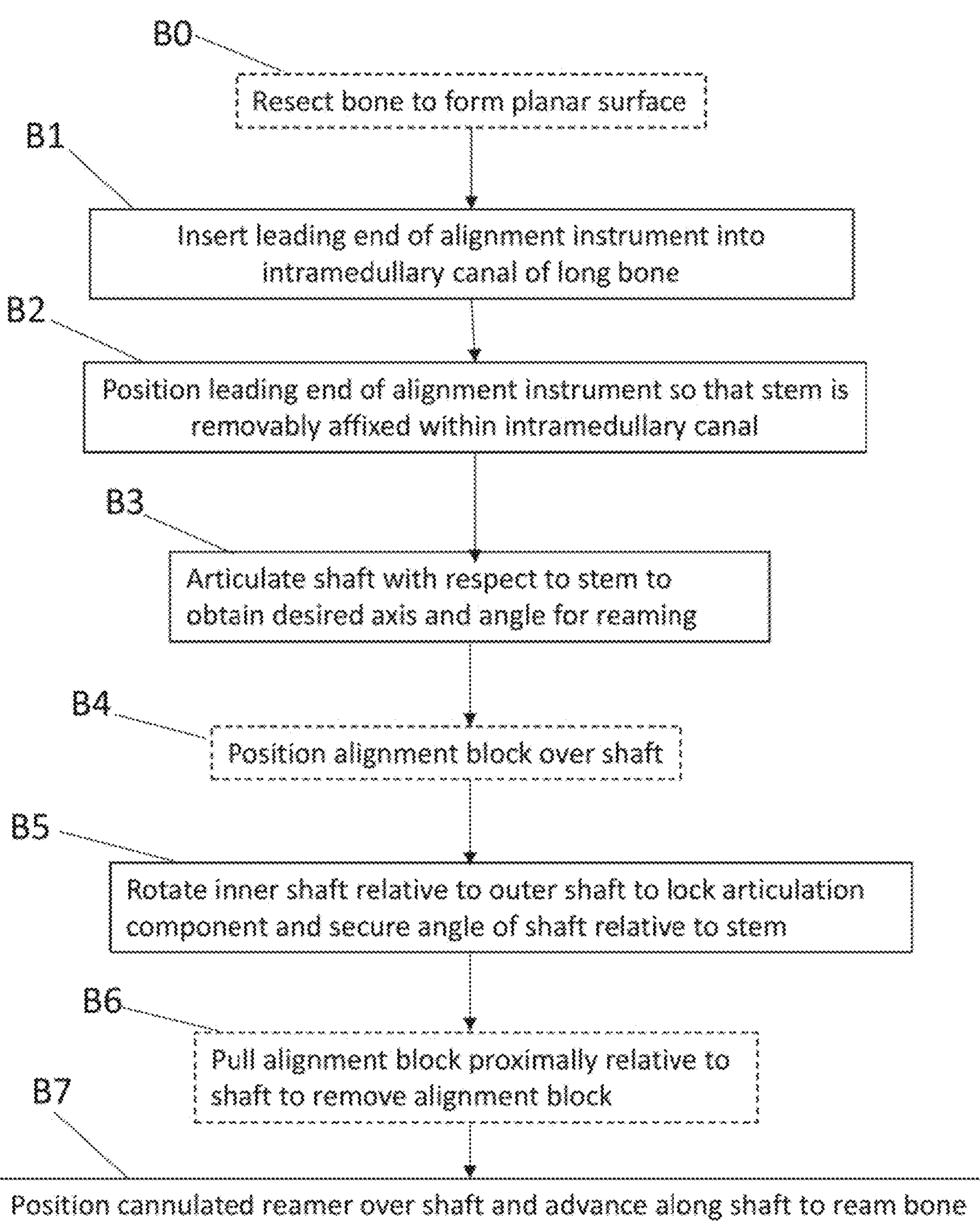
FIG. 12 is a flow chart illustrated a method of using the alignment instrument of FIG. 1.

In one embodiment, a method of assembling alignment instrument 100 is as shown in FIG. 11 and may begin with step A1, with inner shaft 116 being inserted through the cannulation of outer shaft 116 and then threadably engaging inner shaft 116 with outer shaft 116 by rotating inner shaft within the outer shaft until the inner shaft is substantially disposed within the outer shaft. Separately in step A2, cap 130 is positioned over articulation component 140 such that extension component 146 is passed through bore 138 and ball component 144 abuts lip 136. With articulation component 140 disposed therethrough, cap 130 is then threadably coupled to distal portion 115 of outer shaft in step A3 such that ball component 144 is fixed between cap 130 and shaft 110, but still able to rotate and articulate with respect to the cap. In a variation, articulation component 140 may be positioned on end socket 125 of outer shaft 112 and then cap may be placed over articulation component 140 to be threaded onto distal portion 115. In step A4, Stem 150 is then threadably coupled to articulation component 140 by inserting extension component 146 into the interior threaded bore of the stem. After securing cap 130 to outer shaft 112 and securing stem 150 to articulation component 140 as described above, alignment tool 100 is then fully assembled and prepared for use. It is noted that the steps shown in FIG. 11 need not all be performed in the sequence as shown. For example, step A1 may be performed after steps A2-A4 rather than before.

In a fully assembled state, alignment instrument 100 is prepared for insertion into a long bone with stem 150 (e.g. distal end 104) as the leading end and shaft 110 (e.g., proximal end 102) as the trailing end. Prior to the using the alignment instrument, a long bone may be prepared by resecting and drilling an initial bore into the intramedullary canal sized to allow stem 150 to pass therethrough and anchor into the canal of the bone by press fit.

Figure 8:
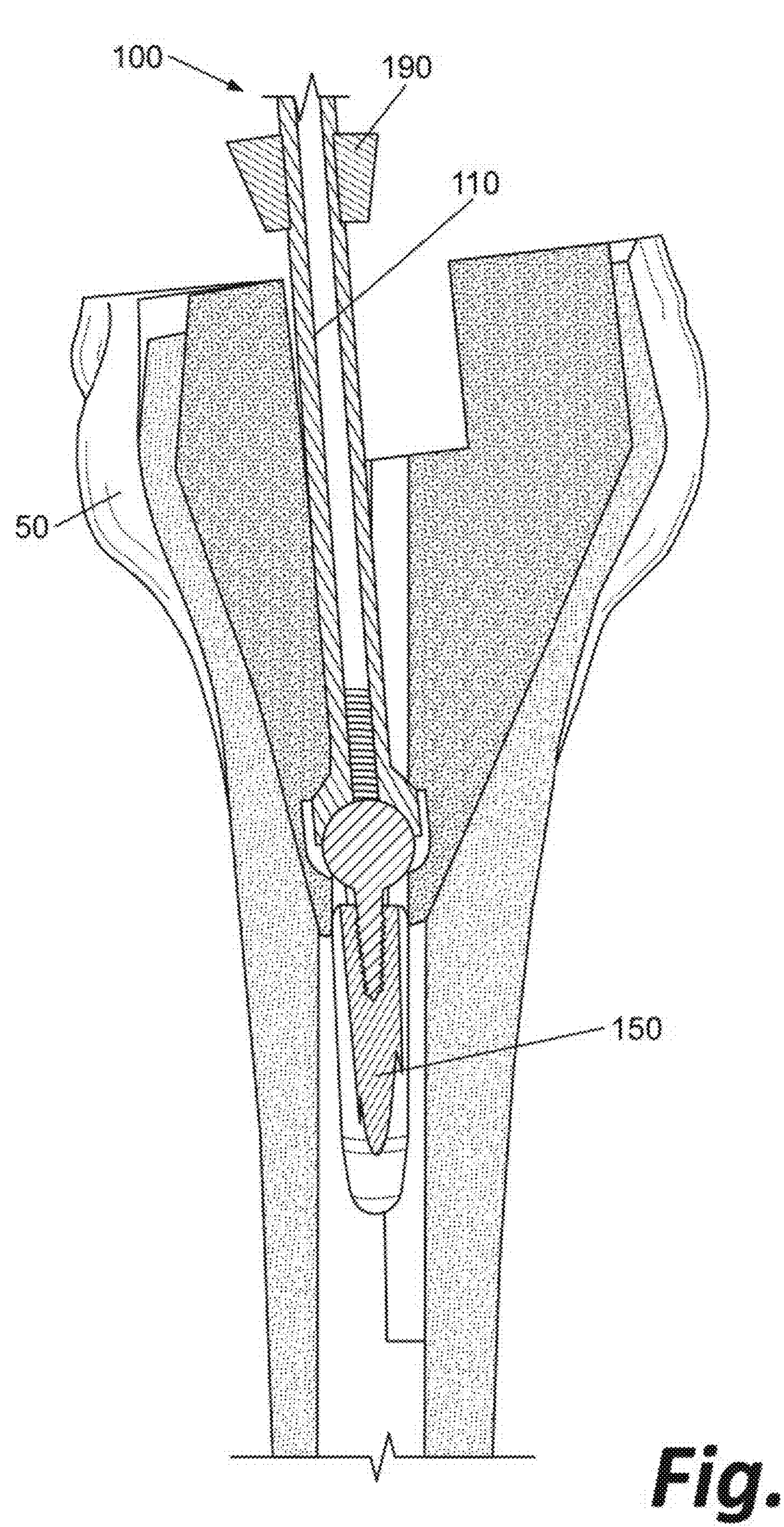
FIG. 8 is side view of the alignment instrument of FIG. 1 positioned in an intramedullary canal of a long bone.

In one embodiment, a method of using alignment instrument 100 may begin with alignment instrument 100 in a fully assembled state as shown in FIG. 1, with the method itself being described with reference to FIGS. 8 and 12. It should be appreciated that steps B0, B4 and B6 are shown in dotted lines as they are optional and may be employed in examples of the method that use an alignment block 180, described in greater detail further below. However, the present example does not include use of alignment block 180, and steps B4 and B6 may therefore be skipped. In step B1, a user, e.g., a surgeon, may grasp any portion of shaft 110, e.g., a portion proximate to proximal end 102, to position stem 150 within an intramedullary canal of a long bone 50, such as a femur. In step B2, the user may then position a leading end of alignment instrument 100 so that stem 150 is removably affixed within the intramedullary canal of long bone 50. In step B3, the angle of the shaft relative to the stem may be adjusted by the user while the anchorage of the stem in the intramedullary canal holds the instrument in place in the long bone. Proximal end 102 of the shaft is moved relative to the stem to obtain a desired angle and direction for reaming Of bone 50. Additionally, the desired angle may be, for example, aligned with an angle at which the implant component will ultimately be inserted into the long bone.

With the alignment instrument 100 assembled and positioned so that stem 150 is received in the intramedullary canal of the bone, alignment instrument 100 is configured to be adjustable between a locked state and an unlocked state. In the unlocked state, articulation component 140 is configured to articulate relative to the shaft 110 with three rotational degrees of freedom as described above. Articulation may be caused by a force applied to shaft 110 relative to stem 150 or by manipulating shaft 110 at oblique angles relative to the direction of the force of gravity, thereby using the weight of the stem to modify the direction in which the stem extends from the shaft. It should be appreciated that such movement between the stem and shaft may be caused by relative movement of the stem as well, though that would not occur when the stem is received in the bone, as is the case in this example of the method. Once the desired angle is achieved in step B3, the user may proceed to step B5 wherein rotation portion 120 of inner shaft 116 may be actuated, e.g., rotated, to advance threaded portion 119 within outer shaft 112 and toward ball component 144. The user may continue to rotate rotation portion 120 until alignment instrument 100 has transitioned from the unlocked state to the locked state, thereby hindering or preventing modification of the angle formed between shaft 110 and stem 150. Such angle may also be referred to as the angle between central longitudinal axis X1 and central longitudinal axis X2, as shown in FIG. 4.

Inner shaft 116 is configured to be rotated via rotation portion 120 relative to outer shaft 112 due to the threaded engagement between the inner and outer shafts. Rotation of inner shaft 116 relative to outer shaft 112 in a first direction, e.g., clockwise, may cause advancement of the inner shaft distally relative to the outer shaft. On the contrary, rotation of inner shaft 116 relative to outer shaft 112 in a second direction opposite the first direction, e.g., counter-clockwise, may cause proximal movement of the inner shaft relative to the outer shaft. In the latter instance, such rotation of inner shaft in the second direction may cause the alignment instrument to transition from the locked state to the unlocked state. Inner shaft 116 is sized to be advanced distally so that threaded portion 119 contacts ball component 144. After contacting ball component 144, inner shaft 116 may be further rotated to increase the pressure applied to the ball component. Upon application of a threshold amount of pressure applied to ball component 144 from both threaded portion 119 and lip 136 of cap 130, the ball component may be hindered or prevented from articulating with respect to shaft 110. Once the threshold amount of pressure is reached to prevent relative movement between shaft 110 and stem 150, alignment instrument 100 is transitioned into the locked state. It should be noted that the greater the pressure applied to ball component 144 between threaded portion 119 and lip 136, the greater the bending moment that must be applied to stem 150 to cause articulation component 140 to articulate. Thus, a maximum level of pressure need not be reached for alignment instrument 100 to be considered in the locked state, so long as at least the threshold amount of pressure is reached such that the position and orientation of shaft 110 relative to stem 150 are maintained without the handling by a user when the alignment instrument is in use. As described above, an outer surface of outer shaft 112 may be contoured to correspond to an interior surface of the hollow reamer 190. In step B7, the hollow cone-shaped reamer 190 may be positioned over proximal end 102 of shaft 110 such that the reamer surrounds the shaft. The reamer 190 may then be advanced along the shaft to ream bone 50. In some examples of the method, translation of the reamer along shaft 110 may be aided by the generally cylindrical shapes of the respective reamer cannulation and shaft 110. A reaming distance may be limited by the shape of the instrument, and in particular, the features proximate the joint. Specifically, the end socket 125 and cap 130 combination may act as a stopper or depth limiter for the reamer to prevent the user from advancing the reamer farther along the shaft in the distal direction than desired.

Figure 10:
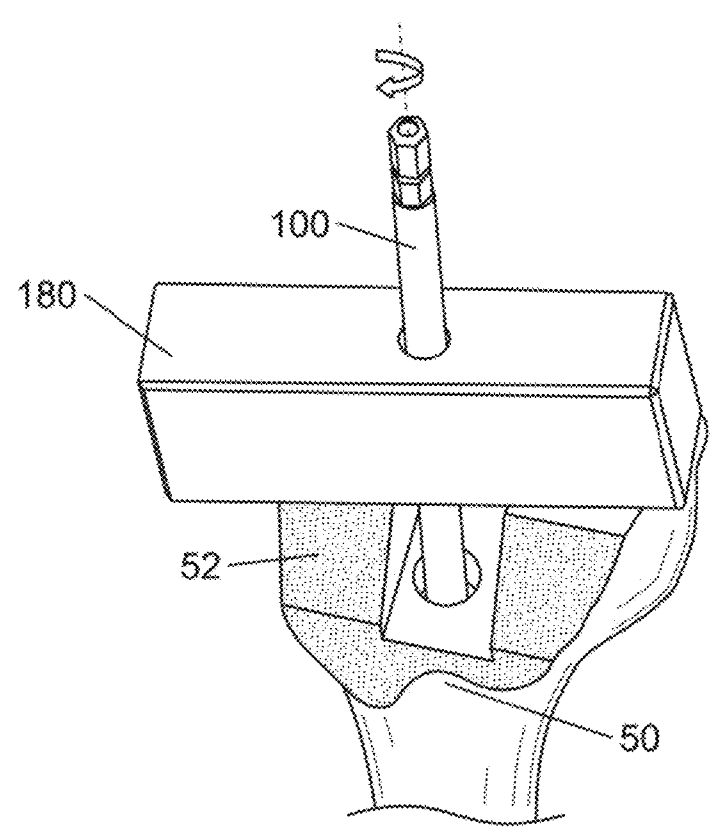
FIG. 10 is a perspective view of the alignment block of FIG. 9 positioned over the alignment instrument of FIG. 1 with the alignment instrument positioned in the long bone.

In some examples of the method of using alignment instrument 100, an alignment block 180 may be implemented in the method of reaming, as shown in FIGS. 9-10 and 12. During the method of use, an end surface 52 of bone 50 may initially be resected to form a substantially planar surface, e.g., on a superior portion of a femur, as indicated in step B0. The surface, or surfaces, of bone 50 may be resected so as to form a planar surface 52 onto which alignment block 180 may be placed. After resection of bone 50 and insertion of alignment instrument 100 into the intramedullary canal as described above, alignment block 180 may be positioned over shaft 110 in step B4 such that block 180 passes entirely over proximal end 102 of the alignment instrument via bore 184. Alignment block 180 may be advanced distally relative to alignment instrument 100 until bone-contacting side 182 of the alignment block contacts resected surface 52. Bone-contacting side 182 and resected surface 52 may extend along parallel planes, i.e., may be flush with each other when alignment block 180 is positioned on bone 50. Thus, because alignment block 180 is substantially flush with resected bone 50 at this stage, the positioning and angle at which alignment block 180 rests is determined by the angle at which resected surface 52 is cut, thereby establishing the desired functional position needed for cone reaming In other words, the desired functional position for cone reaming is an angle and orientation, i.e., radial direction from a longitudinal centerline of the long bone, which will align with the angle and orientation in which a corresponding implant will be inserted into the bone. Prior to or during the operation, a particular positioning and orientation of the implant, such as a femoral component in the illustrated example, may be determined by the surgeon which will produce optimal performance for the patient after implantation therein. Thus, the stability, strength, performance, etc. of the implant may be improved if the space in the bone into which it will be implanted is resected and/or reamed at a corresponding angle. Therefore, the alignment instrument described herein allows for positioning and locking of the angle of the axis (e.g., X1) along which the reamer will be inserted into bone 50 To form a space in the bone into which the implant may be implanted with high performance.

When shaft 110 is positioned within bore 184, central longitudinal axis X1 may align with and may be coincident or parallel with bore axis Y. When the desired position and angle of shaft 110 are achieved relative to stem 150, the shaft may be temporarily locked in the manner described above and shown in step B5, and alignment block 180 may be proximally decoupled from alignment instrument 100 as shown. In step B7, the cone reamer may then be positioned over shaft 110 and may substantially follow longitudinal axis X1 when advanced along the shaft to ream the intramedullary canal of bone 50. After reaming is completed, the cone reamer may be removed and decoupled from shaft 110 by translating the reamer proximally relative to the shaft over proximal end 102. Alignment instrument may be removed from bone 50 while still in a locked condition if possible, or alternatively, may be unlocked by rotating inner shaft 116 relative to outer shaft 112 and removed from the bone thereafter. Finally, the implant may be implanted into the reamed space of the bone.

Although the disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

The invention claimed is:

1. A system comprising:

a hollow reamer; and an alignment instrument comprising:

an outer shaft;

an inner shaft disposed in the outer shaft and translatable within the outer shaft;

an articulation member including a ball component and an extension component extending from the ball component, the ball component being enclosed within an end portion of the outer shaft;

and a stem attached to the extension component, wherein translation of the inner shaft relative to the outer shaft controls locking of the outer shaft relative to the stem, and wherein when the outer shaft is locked relative to the stem, an angle between a central longitudinal axis of the outer shaft and a central longitudinal axis of the stem is fixed, and when the outer shaft is unlocked relative to the stem, the angle between the central longitudinal axis of the outer shaft and the central longitudinal axis of the stem is adjustable, wherein the outer shaft of the alignment instrument has an outer surface contoured to slidably receive a hollow reamer such that when the alignment instrument is disposed in a bone cavity of a bone, the hollow reamer is advanceable over the alignment instrument to cut the bone along a position and orientation of the alignment instrument.

2. The system of claim 1, further comprising an alignment block disposable over the outer shaft of the alignment instrument, the alignment block having a distal surface configured to align the outer shaft based on an external proximal surface of the bone.

3. The system of claim 1, wherein the stem has an outer surface contoured to slidably receive the hollow reamer such that when the alignment instrument is disposed in a bone cavity of a bone, the hollow reamer is advanceable over an entirety of the alignment instrument to cut the bone along a position of the alignment instrument.

4. The system of claim 1, wherein the cap defines an opening sized and shaped to correspond to a distal portion of the shaft.

5. The system of claim 1, wherein the cap includes a lip at a distal end defining a bore sized and shaped to receive the extension component therethrough.

6. The system of claim 1, wherein the stem is threadably coupled to the extension component.

7. The system of claim 1, wherein the inner shaft includes a threaded portion at a distal end thereof adapted to contact the ball component to lock the articulation member.

8. The system of claim 1, wherein the inner shaft includes a rotation portion at a proximal end thereof adapted for actuating the inner shaft relative to the outer shaft.

9. A kit comprising:

the system of claim 1; and a plurality of stems, wherein at least two stems of the plurality of stems have different lengths, each stem of the plurality of stems being adapted to attach to the extension component.

* * * * *